United States Patent [19]

Schmidt

[11] Patent Number: 4,569,133

[45] Date of Patent: Feb. 11, 1986

[54] DEPTH LIMITED CUTTER

[75] Inventor: Friedrich W. Schmidt, Ephrata, Pa.

[73] Assignee: Sharpoint, Inc., Reading, Pa.

[21] Appl. No.: 645,522

[22] Filed: Aug. 28, 1984

Related U.S. Application Data

[63] Continuation of Ser. No. 456,250, Jan. 6, 1983, abandoned, which is a continuation of Ser. No. 203,442, Nov. 3, 1980, abandoned.

[51] Int. Cl.$^4$ .............................................. B26B 29/00
[52] U.S. Cl. ........................................ 30/293; 30/294; 128/305
[58] Field of Search .................... 30/85, 293, 294, 320, 30/77, 79, 286, 287, 288, 289, 2, 165, 296 R, 337, 136; 128/305; 33/174 G, 164 B, 149 C, 149 G, 143 H, 147 G

[56] References Cited

U.S. PATENT DOCUMENTS

| 1,843,535 | 2/1932 | Arnold | 30/293 |
|---|---|---|---|
| 2,601,724 | 7/1952 | Jones | 30/294 |
| 2,743,523 | 5/1956 | Honey | 30/2 |
| 2,934,821 | 5/1960 | Bailey et al. | 30/85 |
| 3,038,254 | 6/1962 | Scheminger | 30/85 |
| 3,608,195 | 9/1971 | Levin | 30/293 |
| 3,740,845 | 6/1973 | Klein | 30/136 |
| 3,945,117 | 3/1976 | Beaver | 30/287 |
| 3,967,377 | 7/1976 | Wells | 30/320 |
| 4,473,076 | 9/1984 | Williams et al. | 30/320 X |

FOREIGN PATENT DOCUMENTS 1121972 1/1962 Fed. Rep. of Germany ........ 30/293

Primary Examiner—Douglas D. Watts
Attorney, Agent, or Firm—Synnestvedt & Lechner

[57] ABSTRACT

A cutting instrument especially adapted for surgical procedures that includes structure for readily determining the cutting depth of the blade of the instrument. The structure includes a longitudinally moveable slide that carries a depth-determining shoe at its outer end. The longitudinal position of the slide is controlled by a rotatable ferule mounted on the handle of the instrument. The construction is particularly adapted for disposable, single-use instruments.

8 Claims, 15 Drawing Figures

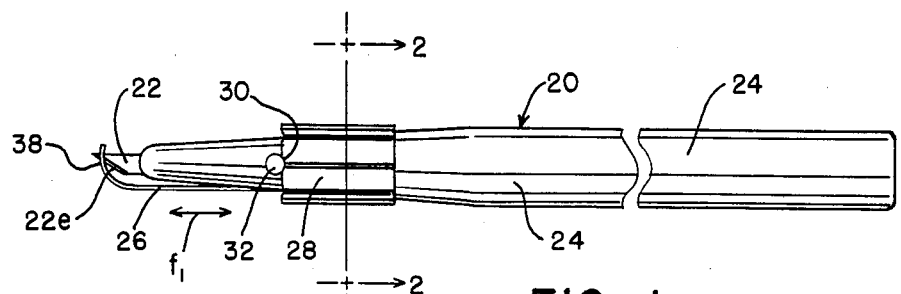
FIG. 1
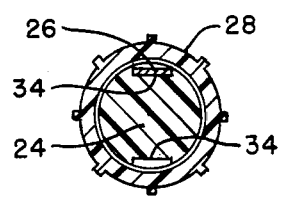
FIG. 2
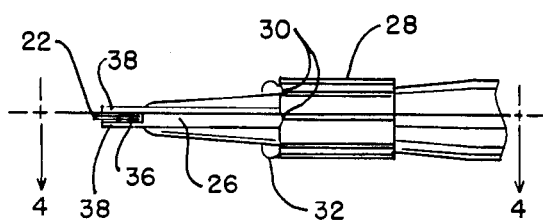
FIG. 3
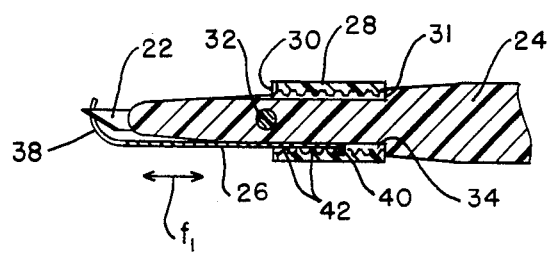
FIG. 4
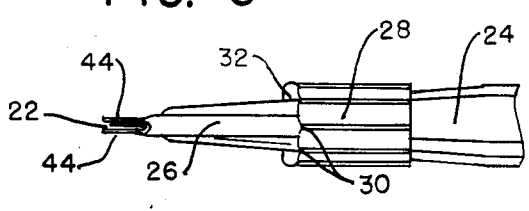
FIG. 6
FIG. 5

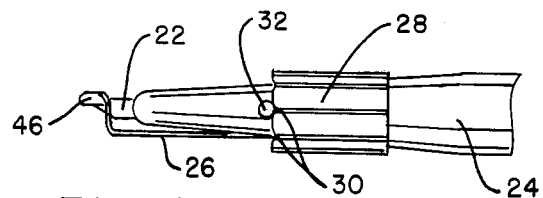
FIG. 7
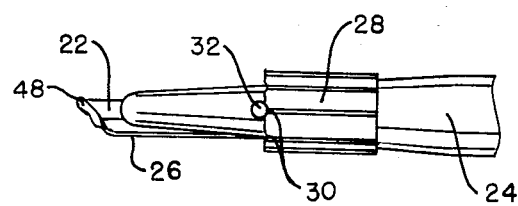
FIG. 8
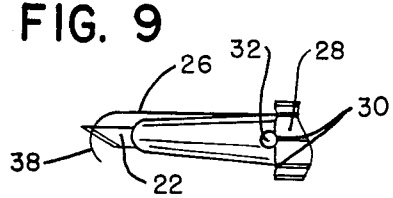
FIG. 9
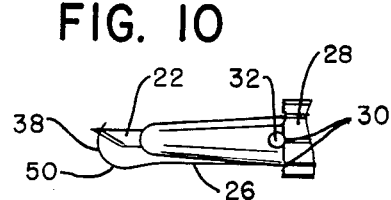
FIG. 10
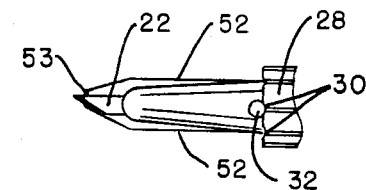
FIG. 11
FIG. 12
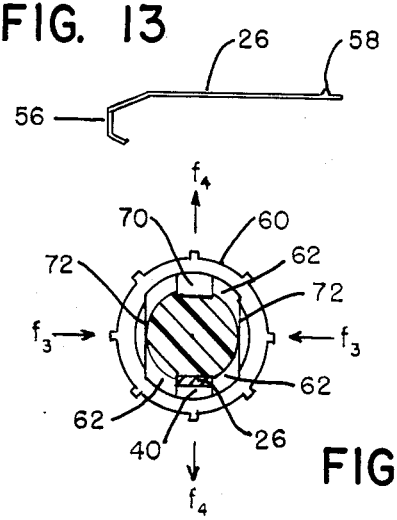
FIG. 13
FIG. 15
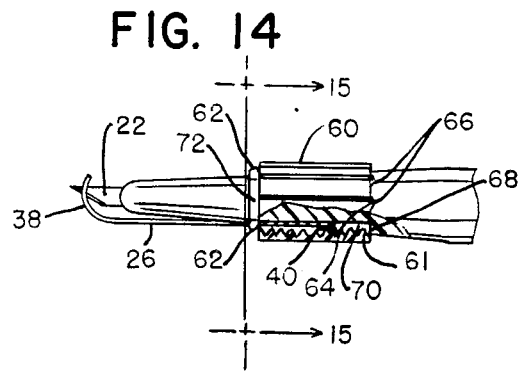
FIG. 14

DEPTH LIMITED CUTTER

This application is a continuation of application Ser. No. 456,250, filed Jan. 6, 1983, now abandoned, which is a continuation of application Ser. No. 203,442, filed Nov. 3, 1980, now abandoned.

BACKGROUND OF THE INVENTION

1. Field of the Invention

This invention relates to cutting instruments and particularly to knives that are used for performing surgical procedures.

2. Background Discussion

Recently, several micro-surgical procedures have been developed that call for the surgeon to make incisions to very closely controlled depths. An example of such surgery is the radial keratotomy techniques presently being developed to reduce or eliminate myopia. These procedures require that a plurality of incisions be made in the cornea of the eye, commonly to a depth on the order of 0.5 mm to 0.6 mm. If these incisions are made too deep, serious damage to the eye can result.

3. Description of Known Prior Developments

Several systems have been proposed for mechanically controlling the depth of the surgeon's incision. U.S. Pat. No. 2,932,296 to Sanders shows a blade receiving appliance that is primarily used for guiding the direction of large incisions and that, incidentally, functions as a control of the cutting depth. Such apparatus may be useful in general surgery but is not believed to be useful in the majority of microsurgical techniques that are performed under a microscope and on a generally small-sized surgical field. Also, the surgeon desires to keep the cutting edge in constant view while the cutting is performed so that maximum control can be exercised. The structure proposed in the above-noted patent would tend to make such observation of the cutting edge difficult.

Another solution proposed is to use a stop element that is frictionally mounted on the blade prior to the procedure, as shown in U.S. Pat. No. 3,945,117 to Beaver. This system requires the use of a separate, sterilely maintained gauge element for setting the stop at the proper position. With this type of depth control, resetting the stop during a procedure can be time-consuming and awkward.

Another method of controlling blade depth involves the use of a blade gauge that is used in conjunction with a blade holder and separable cutting blades that are freely positioned in the holder. In such an approach, the holder is moved along a flat surface and the distance from the tip of the holder to the tip of the blade is noted from a graduated measuring line. However, the guide merely functions to indicate proper cutting depth and does not include means for varying the position of the blade. Further, there is a risk of damaging the cutting edge by contact with the gauge as the exposure is being measured.

Depth control of cutting blades has been accomplished in fields other than surgery. A knife having a cutting depth control feature is shown in U.S. Pat. No. 1,843,535 to Arnold. However, the arrangement shown in this patent does not provide for fine adjustment of the position of the stop element and requires the use of additional tools for resetting and locking the stop element in a desired position. It is believed that these factors would limit the acceptability of this design for surgical use.

SUMMARY OF THE INVENTION

The invention disclosed yields a knife design that provides a readily adjustable, easily determinable means for controlling the amount of exposure of the cutting edge, thereby providing for precise control of the cutting depth of the blade. In addition, the design provides protection to the cutting edge during handling and packaging.

These desirable attributes stem from the use of a shoe or stop element that moves relative to the blade to expose a desired length of the cutting edge. Control mechanism, for controlling the position of the shoe with respect to the cutting edge, is mounted on the knife. In a preferred arrangement, the blade shoe is mounted for sliding movement that is effected by rotation of a rotatable positioning member that rotates about a longitudinal axis of the knife handle.

DESCRIPTION OF THE DRAWING

FIG. 1 is a side elevation of a micro surgical knife employing the invention.

FIG. 2 is a cross sectional view of the knife shown in FIG. 1 taken along line 2—2.

FIG. 3 is a bottom view of the distal, or blade carrying, end of the knife shown in FIG. 1.

FIG. 4 is a cross sectional view taken along line 4—4 of FIG. 3.

FIG. 5 is a side elevational view of the fore portion of a knife employing a flat bladed shoe structure that is different from that shown in FIGS. 1-4.

FIG. 6 is a top view of the embodiment shown in FIG. 5.

FIGS. 7 and 8 show alternate forms of shoe structure depicted in FIGS. 5 and 6.

FIG. 9 illustrates an alternate positioning of the blade shoe of the embodiment of FIGS. 1-4.

FIG. 10 shows a modified form of shoe structure having an enlarged shoe surface.

FIG. 11 demonstrates another form of shoe structure having a generally U shape.

FIG. 12 is a top view of the FIG. 11 embodiment.

FIG. 13 shows another blade shoe shape.

FIG. 14 depicts a second form of adjusting structure employing a raised rib for retaining the adjustment member.

FIG. 15 is a cross sectional view taken along line 15-15 of FIG. 14.

DESCRIPTION OF THE PREFERRED EMBODIMENT

Although the invention described in this application is believed to have applicability to a wide range of hand-held knives, its initial development has taken place in the context of micro surgical knives or scapels. Therefore, the following description, without limiting intent, is cast in the context of surgical knives.

FIG. 1 shows a surgical knife 20 that comprises a suitable blade 22, having a cutting edge 22e, and a handle 24 in which the blade is fixed. Knives of this basic type are commercially available and no further description is believed necessary.

A blade exposure or depth-of-cut control means is mounted on the knife 20. In the embodiment shown in FIG. 1, such means includes a movable member 26 that is slideable with respect to handle 24. The member 26 has shoes or stop elements 38 that are smooth surfaced and polished, as they are designed to engage tissue. Member 26 is preferably made of a substantially rigid material, such as stainless steel or a rigid synthetic polymeric material. The member 26, as shown in greater detail in FIGS. 2 and 4, slides longitudinally with respect to handle 24 in a slot or slots 34 formed in the handle 24.

The structure in the preferred embodiment of FIG. 1 for regulating the position of member 26 includes a generally cylindrical sleeve or ferrule 28 that is mounted for rotation about the longitudinal center line axis of handle 24. The rotatable member 28 is axially retained on handle 24 by the shoulder 31 at one end (see FIG. 4) and a transversely extending pin 32 at the opposite end. The sleeve 28 overlies at least a portion of the slots and serves to retain the slideable member 26 in ones of the slots 34. A continuous helical groove 42 is formed on the interior surface of the sleeve 28, conveniently in the form of screw threads.

The slideable member 26 includes suitable means, for example an upstanding tang or nib 40 that rides in the helical slot 42. It will be readily apparent that as the sleeve 28 is rotated, the tang or nib 40, thus the member 26 and shoes 38, will be moved in a longitudinal direction, as indicated by arrow $f_1$, depending upon the direction of rotation of the sleeve and the pitch of the groove 42. By carefully chosing the groove pitch, a given amount of rotation of sleeve 28 can be related to a convenient amount of linear shoe travel. For example, one complete revolution of sleeve 28 can result in approximately 0.5 mm of travel of shoe 38, so that, assuming the shoe is positioned at the tip of the cutting edge at the start, a blade length of 1 mm will be revealed.

In some surgical techniques, it is useful to be able to control cutting depth to fractions of a millimeter, to accomplish this, a detent mechanism is included in the design shown. This mechanism includes a plurality of equally spaced detent grooves 30 formed in the edge of sleeve 28 adjacent the pin 32. The grooves 30 cooperate with the outwardly extending portions of the pin 32 to give a detectable click or detent action as the sleeve is rotated. By counting or visually observing the number of "clicks", the surgeon can set a precise blade exposure. The sleeve 28 and/or pin 32 are made of a sufficiently yieldable material, for example a synthetic plastic so that the sleeve can rotate readily, yet the pin will coact with grooves 30 to give the desired detent action.

FIG. 2 shows that the handle 24 has two diametrically opposed slots 34. This is important for manufacturing convenience so that the member 26 can be placed with the shoes 38 extending upwardly from the bottom of the blade (FIGS. 1 and 4) or with the shoes 35 extending downwardly from the top of the blade as shown in FIG. 9.

Referring to FIG. 3, the movable guard member 26 can carry a pair of shoes 38 that are formed by the slot 36 through which blade 22 extends. Alternatively, only one such shoe 38 may be provided, especially in situations where it is desirable for the surgeon to have a completely unobstructed view of the blade from one side.

In the FIGS. 5 and 6 embodiment, the guard member 26 carries a somewhat differently formed shoe structure. Here, penetration control is provided by one or a pair of flat plates 44 that are positioned closely adjacent the bade cutting edge. The tip ends of plates 44 are suitably shaped and/or polished to avoid causing additional trauma to the wound edges. The adjustment of the position of plates 44 is accomplished in the same manner as described in connection with FIGS. 1-4. This design has the advantage of allowing the entire cutting edge of the blade to be observed. FIG. 7 shows a varient of the design shown in FIGS. 5 and 6. In this embodiment the slideable member 26 extends along the bottom of the knife and the side plates 46 are positioned in adjacent to the cutting edge of blade 22 in the manner as shown. FIG. 8 shows a modification of the FIG. 7 arrangement employing side plates 48 that are shaped somewhat differently.

FIG. 10 illustrates a guard member 26 that includes a double bend arrangement. In this form, the guard is extended away from the knife blade, as at section 50, and the shoes 38 extend toward the blade 22. This allows the shoes 38 to have a larger radius, in comparison to the forms shown in FIGS. 1-4 and 9, thereby allowing more of the shoe 38 to be in contact with the tissue against which the blade is placed.

FIGS. 11 and 12 illustrate a U-shaped slideable member having a pair of opposed legs 52 positioned in slots 34 (See FIG. 2). The legs 52 are joined by a curved shoe surface 53 that has a slit 54 through which the blade can extend. The positioning of the slideable member is accomplished in the same manner as embodiments previously discussed.

FIG. 13 illustrates a modification to the FIGS. 1-4 and FIG. 9 type guards. This form employes a substantially flat shoe 56. It further illustrates the use of a raised nib 58 that is positioned and shaped to be engaged in the internal helical groove of a sleeve 28.

FIGS. 14 and 15 set forth another possible arrangement for retaining a sleeve 60 on the handle 24. Here, the handle has a retaining rib 62 that can be integrally formed with the handle. The rib is generally circular but includes a pair of opposed flats 72. The sleeve 60 is formed of a somewhat flexible but resilient material, for example, a synthetic polymeric material. The sleeve 60 is placed on the handle by squeezing the sleeve in the directions of arrows $f_3$ (FIG. 15). This in turn causes the cross section of the sleeve to expand on its unrestrained sides, as shown by arrows $f_4$ (FIG. 15). When held in this configuration, the sleeve can be slipped over the retaining rib 62. After the force on the sleeve is relaxed, the sleeve returns to its original circular cross section and the retaining rib serves to retain the sleeve against axial movement but allows the sleeve to rotate with respect to handle 24.

The sleeve 60 has an internal helical channel, as in the FIG. 1 embodiment, that receives the nib 40 of the slideable member 26. Rotation of sleeve 60 caused longitudinal movement of member 26, that is held in slot 70 by the sleeve 60. Thus movement of member 26 results in the same manner as the previously described embodiments. Detenting of rotation of sleeve 60 can be accomplished in several ways, the one shown utilizing a detent nib 64 on the sleeve 60 that is shaped to engage a plurality of detent slots 66 formed in the shoulder 68 of handle 24.

Having described the physical structure of the cutting instrument, its use and functioning is believed evident. The various forms of shoes 38 serve to limit the cutting depth of the blade to the portion of the blade that extends beyond the shoe or shoes. A further advantage of this construction is that at the time of assembly of the knife, the guard member can be positioned with the shoes positioned just at the tip of the blade or slightly beyond it. Thus, the blade is protected against damage during subsequent manufacturing and packaging stages.

A very desirable feature of the structure disclosed is that the entire guard setting mechanism is hand actuable. That is, the guard can be set at the desired position by the user without the need for ancillary tools. This reduces the complications of maintaining sterility that are introduced by the necessity of such ancillary equipment.

I claim:

1. A hand held cutting instrument comprising
   an elongate handle,
   a blade mounted at an end of the handle, said blade having a longitudinally outwardly extending cutting edge disposed along at least one edge thereof,
   guard means disposed adjacent the blade for limiting the length of cutting edge exposed for use,
   a sleeve member mounted for hand actuated rotation about the longitudinal central axis of the handle, said sleeve being positioned adjacent the blade end of the handle and axially retained thereon in a longitudinally fixed position that overlies a portion of the guard means, and
   adjustment means interconnecting the sleeve member and the guard means for setting the guard means in a plurality of longitudinal positions with respect to the handle and the blade to expose predetermined lengths of the cutting edge by rotating the sleeve member about the longitudinal axis of the handle.

2. An instrument as in claim 1 wherein the handle is provided with stopping means preventing axial movement of the rotatable member relative to the longitudinal handle axis.

3. An instrument as in claim 2 wherein the sleeve member includes an axially extending helical groove and the guard means is slideable with respect to the blade and handle and includes means for engaging the groove in the rotatable member.

4. An instrument as in claim 1, 3 or 2 wherein the guard means includes a pair of curved shoes, one on each side of the blade.

5. An instrument as in claim 1, 3 or 2 wherein the guard means comprises a pair of flat shoes, one on each side of the blade.

6. An instrument as in claim 1, 3 or 2 wherein the guard means comprises a U-shaped member having a pair of opposed legs movable longitudinally with respect to the handle and joined by a shoe section positioned adjacent the blade cutting edge.

7. An instrument as in claim 3 or 2 wherein the sleeve member includes detent means for positioning the member in a plurality of angular positions, the detent means further including a pin extending transversely through the handle and in engagement with the rotatable member.

8. An instrument as in claim 3 or 2 wherein the handle includes an oval-shaped raised rib for axially retaining the rotatable member on the handle.

* * * * *